United States Patent
Cotter et al.

(10) Patent No.: US 9,420,819 B2
(45) Date of Patent: *Aug. 23, 2016

(54) NUTRITIONAL FORMULATION

(75) Inventors: Richard Cotter, Mendham, NJ (US); Randy Stodard, Bay Head, NJ (US)

(73) Assignee: Wyeth LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/565,986

(22) Filed: Aug. 3, 2012

(65) Prior Publication Data

US 2012/0294983 A1 Nov. 22, 2012

Related U.S. Application Data

(63) Continuation of application No. 12/226,395, filed as application No. PCT/US2007/008132 on Apr. 3, 2007, now abandoned.

(60) Provisional application No. 60/744,301, filed on Apr. 5, 2006.

(51) Int. Cl.
| | |
|---|---|
| *A23L 1/303* | (2006.01) |
| *A23L 1/304* | (2006.01) |
| *A23L 1/30* | (2006.01) |
| *A23L 1/302* | (2006.01) |
| *A61K 9/20* | (2006.01) |

(52) U.S. Cl.
CPC .............. *A23L 1/3002* (2013.01); *A23L 1/302* (2013.01); *A23L 1/303* (2013.01); *A23L 1/304* (2013.01); *A61K 9/20* (2013.01)

(58) Field of Classification Search
CPC ......... A61K 9/20; A23L 1/302; A23L 1/303; A23L 1/304; A23L 1/3002
See application file for complete search history.

(56) References Cited

U.S. PATENT DOCUMENTS

| | | | |
|---|---|---|---|
| 5,976,568 A | 11/1999 | Riley | |
| 2005/0214383 A1* | 9/2005 | Bubnis et al. | ............... 424/641 |
| 2005/0249820 A1* | 11/2005 | Alam | ............................ 424/638 |

FOREIGN PATENT DOCUMENTS

| | | |
|---|---|---|
| DE | 94 12 374 U1 | 9/1994 |
| DE | 203 10 493 U1 | 10/2003 |
| WO | WO 02/47493 A2 | 6/2002 |

* cited by examiner

*Primary Examiner* — Abigail Fisher
*Assistant Examiner* — Daniel Branson
(74) *Attorney, Agent, or Firm* — Jeffrey M. Gold; Maureen P. O'Brien; Paula K. Davis

(57) ABSTRACT

The present invention relates to nutritional supplements that provide an adult with essential vitamins and minerals that may be lacking in the adult's diet and prevent chronic diseases, such as osteoporosis. A number of combinations of nutrients in set ratios are provided to increase the body's ability to absorb and use the nutrients. These combinations are important in helping the body reach the proper balance required for maximized function. Because adults over the age of 50 years have different nutritional needs, nutritional supplements specifically designed for them are also provided.

6 Claims, No Drawings

NUTRITIONAL FORMULATION

FIELD OF THE INVENTION

The present invention relates to nutritional supplements for adults, including those over the age of 50.

BACKGROUND OF THE INVENTION

In order to remain healthy, men and women of all ages need to intake certain amounts of various nutrients. An adult deficient of one or more of these nutrients is more susceptible to various disorders, such as osteoporosis and heart disease. As a result, adults frequently supplement their diets with multi-vitamins to inhibit, prevent, or reduce the frequency or severity of these disorders.

In order to maximize patient compliance, multi-vitamins are typically formulated to require daily administration of only one solid dosage form. Of course, the size of the dosage form is of great importance, as a tablet or capsule which is so large as to be difficult to swallow and digest will reduce patient compliance. Consequently, the amount of vitamins, minerals, and other nutrients included in the dosage form is limited by the desired size of the dosage form.

Many different multi-vitamin compositions are currently manufactured and sold in the United States. They range in content from a few ingredients to more than 30. However, it has been found that it is not sufficient that ingredients be ingested randomly. Instead, it has been shown that it is beneficial to ingest certain ingredients in the presence of others. For example, it is known that the presence of Vitamin D aids in the absorption of calcium and its preventative action against osteoporosis.

However, it is also known that the simple concurrent ingestion of nutritional ingredients does not always guarantee increased efficacy. For example, U.S. Pat. No. 4,431,634 to Ellenbogen discloses that the absorption of iron from a nutritional supplement can be negatively impacted by the presence of certain concentrations of other metal salts, such as those containing calcium or magnesium.

Therefore, it is an object of the present invention to provide unitary dose nutritional supplements for once daily administration offering improved nutrient benefits.

It has been discovered that the administration of combinations of certain nutrients in set ratios increase the body's ability to absorb and use such nutrients. These combinations are important in helping the body reach the proper balance required for maximized function and/or good health.

SUMMARY OF THE INVENTION

The present invention is directed to a nutritional supplement having vitamin D, copper sulfate and chromium picolinate. The nutritional supplement is adapted to provide nutritional elements including about 200-700 IU vitamin D, about 0.6-1.2 mg copper, and 0.03-0.15 mg chromium. The supplement contains cholecalciferol, copper sulfate and chromium picolinate to provide the nutritional elements. The supplement may also contain zinc in an amount such that the supplement has a zinc to copper ratio of about 1.1-1.4.

In another embodiment, the present invention is directed to a nutritional supplement having microspheres of lutein, lycopene and beta-carotene wherein the lutein, lycopene and beta-carotene are present in a ratio of about 1-1.9 (mcg):1.3-2.1 (mcg):1.4-4.3 (IU).

In yet another embodiment, a nutritional supplement is provided for adults over the age of 50 years of age to meet different nutritional needs of the age group.

DETAILED SUMMARY OF THE INVENTION

One or more of the embodiments below may be combined in order to provide a unitary nutritional supplement containing the nutrients from each embodiment in the amounts specified. Unless indicated otherwise, the combinations below are for nutritional supplements for adults of all ages as well as adults over the age of 50.

Vitamin D3, Copper Sulfate, and Chromium Picolinate

According to one embodiment of the present invention, the nutritional supplement includes vitamin D3 (cholecalciferol), copper sulfate and chromium picolinate. This particular combination of nutrients results in improved absorption, bioavailability, and metabolism of vitamin D, copper, and chromium compared to prior art combinations, such as the combination of copper oxide, chromium chloride, and vitamin D2. The vitamin D helps muscle, nerve, and bone by promoting absorption of calcium and affecting muscle and nerve metabolism. The chromium improves glucose metabolism and decreases the risk of diabetes, especially for those over the age of 50.

Preferably, the ratio of vitamin D3, copper sulfate and chromium picolinate in the nutritional supplement is about 1540-5385 (IU):11.5-23.1 (mg):1-3.9 (mg). More preferably, the ratio is about 200-700 IU vitamin D3, about 1.0-3.0 mg copper sulfate, and about 0.13-0.51 mg chromium picolinate. According to one preferred embodiment, the nutritional supplement includes about 400 IU vitamin D3, about 2.52 mg copper sulfate (based on monohydrate), and about 0.28 mg chromium picolinate. According to another preferred embodiment, the nutritional supplement is intended for adults over the age of 50 and includes about 500 IU vitamin D3, about 2.25 mg copper sulfate, and about 0.36 mg chromium picolinate. According to another embodiment, the nutritional supplement includes vitamin D, elemental copper and elemental chromium at a ratio of about 330-1170 vitamin D (IU):1-2 copper (mg):0.05-0.25 chromium (mg), preferably at a ratio of about 667 vitamin D (IU):1.5 copper (mg):0.058 chromium (mg) for a supplement formulation suitable for the age group under 50, and preferably at a ratio of about 833 vitamin D (IU):1.5 copper (mg):0.075 chromium (mg) for a supplement formulation suitable for the age group over 50. For a physically active individual, a preferred embodiment has the ratio of about 667 vitamin D (IU):1.5 copper (mg):0.2 chromium (mg).

Preferably, the nutritional supplement further includes vitamin E. The vitamin E enhances the anti-oxidant properties of the supplement. This combination provides maximal bioavailability of these key nutrients to prevent deficiency, reduce insulin resistance, help carbohydrate metabolism, weight control, bone, muscle, and neuronal dystrophies maximize antioxidant protection, provide neuronal benefits, and reduce the risk of chronic diseases, including diabetes, cancer, muscular dystrophy, and heart disease. The weight ratio of vitamin D3, copper sulfate, chromium picolinate and vitamin E is preferably about 1540-5385 (IU):11.5-23.1 (mg):1-3.9 (mg):115-462 (IU). More preferably, the nutritional supplement includes about 200-700 IU vitamin D3, about 1.0-3.0 mg copper sulfate, about 0.13-0.51 mg chromium picolinate, and about 1560 IU vitamin E. According to one preferred embodiment, the nutritional supplement includes about 400 IU vitamin D3, about 2.52 mg copper sulfate, about 0.28 mg chromium picolinate, and about 30-60 IU vitamin E. According to another preferred embodiment, the nutritional supplement is intended for adults over the age of 50 and includes about 500 IU vitamin D3, about 2.52 mg copper sulfate, about 0.36 mg chromium picolinate, and about 50 IU vitamin E. According to another embodiment, the nutritional supplement includes about 400 IU vitamin D, about 0.9 mg elemental copper, about 0.035-0.12 mg elemental chromium and about 30-60 IU vitamin E.

Beta-Carotene and Vitamin A

Another embodiment is a nutritional supplement for adults over the age of 50 which contains vitamin A (retinol) and beta-carotene (a precursor to vitamin A) at a ratio (IU:IU) of from about 1:1 to about 3:1 and more preferably from about 1.5:1 to about 2.45:1. According to a preferred embodiment, the ratio is about 1.5:1.

Preferably, the nutritional supplement includes from about 1300-2700 IU vitamin A and about 800-1200 IU beta-carotene, preferably about 900-1100 IU beta-carotene. According to one embodiment, the nutritional supplement is intended for adults over the age of 50 and includes about 1500 IU vitamin A and about 1000-1100 IU beta-carotene, preferably about 1000 IU beta-carotene. As for a nutritional supplement intended for adults under the age of 50, it may include about 2500 IU vitamin A and about 1000-1100 IU beta-carotene, preferably about 1000 IU beta-carotene.

There has been increasing concern that vitamin A increases the risk of developing chronic bone diseases, such as osteoporosis. This ratio of vitamin A and beta-carotene minimizes the risk of developing such diseases while preventing vitamin A deficiencies.

Zinc and Copper

Yet another embodiment is a nutritional supplement containing zinc and copper at a weight ratio of about 450-650: 30-60. This combination maximizes absorption of the zinc and copper, while minimizing the risk of possible negative cardiovascular side effects due to their interaction. A preferred embodiment of the nutritional supplement includes about 9-13 mg zinc and about 0.6-1.3 mg copper. Preferably, zinc and copper are present in a zinc to copper ratio between about 1.1 and 1.4, based the total weight of the two elemental metals in the supplement. A more preferred embodiment of the nutritional supplement includes about 11 mg zinc and about 0.9 mg copper, providing a supplement formulation with a zinc to copper ratio of about 1.22.

Desirably, the nutritional supplement includes zinc, molybdenum, copper and chromium at a weight ratio of about 450-650:1.5-3:30-60:1-3. The nutritional supplement preferably includes about 9-13 mg zinc, about 30-75 mcg molybdenum, about 0.6-1.3 mg copper, and about 35-120 mcg chromium. According to one preferred embodiment, the nutritional supplement includes about 11 mg zinc, about 45 mcg molybdenum, about 0.9 mg copper, and about 35 mcg chromium. According to another preferred embodiment, the nutritional supplement is intended for adults over the age of 50 and includes about 11 mg zinc, about 45 mcg molybdenum, about 0.9 mg copper, and about 45 mcg chromium.

The nutritional supplement also desirably includes calcium, zinc, copper, magnesium, and manganese at a weight ratio of about 179-421:11.4-20:1-1.6:36-214:2.7-3.9. This combination promotes optimal absorption of these nutrients. Preferably, the nutritional supplement includes:
    about 90-295 mg calcium, about 8-14 mg zinc,
    about 0.7-1.1 mg copper,
    about 25-150 mg magnesium, and about 1.9-5 mg manganese.

According to one preferred embodiment, the nutritional supplement includes:
    about 200 mg calcium, about 11 mg zinc,
    about 0.9 mg copper,
    about 100 mg magnesium, and about 2.3 mg manganese.

According to another preferred embodiment, the nutritional supplement is intended for adults over the age of 50 and includes: about 220 mg calcium,
    about 11 mg zinc,
    about 0.9 mg copper,
    about 50 mg magnesium, and
    about 2.3 mg manganese.

The nutritional supplement may further include iron. Preferably, the weight ratio of calcium, zinc, copper, magnesium, manganese and iron is about 179-421:11.4-20:1-1.6:36-214:2.7-3.9:17.2-34.3. A preferred embodiment of the ironcontaining nutritional supplement includes:
    about 90-275 mg calcium,
    about 8-14 mg zinc,
    about 0.7-1.1 mg copper,
    about 25-150 mg magnesium, about 1.9-5 mg manganese,
        about 12-24 mg iron.

A more preferred embodiment of the iron-containing nutritional supplement includes:
    about 200 mg calcium,
    about 11 mg zinc,
    about 0.9 mg copper,
    about 100 mg magnesium, about 2.3 mg manganese, and
        about 18 mg iron.

Lutein, Lycopene and Beta-Carotene

Yet another embodiment of the present invention IS a nutritional supplement containing lutein, lycopene and beta-carotene. Preferably, the nutritional supplement includes micro spheres containing, either separately or together, the lutein, lycopene and beta-carotene (such as those available from BASF Ag of Florham Park, N.J. and DSM Nutritional Products, Inc. of Belvidere, N.J.). In other words, the nutritional supplement may include micro spheres, each of which contains lutein, lycopene and beta-carotene, or, alternatively, micro spheres, each of which only contains one of lutein, lycopene and beta-carotene (e.g., micro spheres containing lutein would not contain lycopene or beta-carotene).

The ratio of lutein, lycopene and beta-carotene is typically about 1-1.9 (mcg):1.3-2.1 (mcg):1.4-4.3 (IU). This combination of antioxidants helps support the natural cell repair process and prevents cell damage resulting in chronic diseases of oxidative origins, such as age-related macular degeneration. Furthermore, the specified ratio of lutein, lycopene and beta-carotene prevents them from competing with one another in order to maximize absorption and bioavailability. The lutein protects against cataracts and macular degeneration, while the lycopene enhances heart health and reduces the risk of heart disease.

Preferably, the nutritional supplement includes about 200-650 mcg lutein, about 250-750 mcg lycopene, and about 500-1500 IU beta-carotene. A more preferred embodiment of the nutritional supplement includes about 250 mcg lutein, about 300 mcg lycopene, and about 1000 IU beta-carotene.

The beta-carotene, lycopene, and lutein may be in a mixture as described in U.S. Pat. No. 6,509,029, which is hereby incorporated by reference. The nutritional supplement preferably contains micro spheres containing beta-carotene, lycopene, and lutein. Providing these nutrients in the form of microspheres ensures that a specific ratio of these nutrients in the supplement is maintained. The specific ratio prevents these nutrients from competing with one another, and allows for maximum absorption of the nutrients.

Calcium and Phosphorous

Yet another embodiment is a nutritional supplement containing calcium and phosphorous at a weight ratio of about 1.75:1 to about 2.25:1 and more preferably at about 2:1. This weight ratio of calcium to phosphorous optimizes the absorption of the calcium.

According to one preferred embodiment, the nutritional supplement includes about 180-220 mg calcium and about 90-120 mg phosphorous, although low levels of phosphorous can be used. According to another preferred embodiment, the nutritional supplement is intended for adults over the age of 50 and includes about 210-230 mg calcium and about 105-115 mg phosphorous. According to one preferred embodiment, the nutritional supplement includes about 200 mg calcium and about 109 mg phosphorous. According to another preferred embodiment, the nutritional supplement is intended for adults over the age of 50 and includes 220 mg calcium and about 110 mg phosphorous.

Vitamin C, Vitamin K, Folic Acid, Calcium, Selenium, Manganese, Lutein and Lycopene Yet another embodiment is a nutritional supplement including vitamin C, vitamin K, folic acid, calcium, selenium, manganese, lutein and lycopene at a weight ratio of about 3000-4200:1-3.4:20-28:7600-9200:1.6-2.8:86-98:14-26:18-30. The calcium and vitamin K help bone health (e.g., maintain strong bones), while the vitamin C enhances the anti-oxidant properties of the supplement. The folic acid helps prevent anemia, osteoporosis, certain cancers as well as fatigue and acne.

Preferably, the nutritional supplement includes: about 75-130 mg vitamin C,
about 25-85 mcg vitamin K,
about 300-700 mcg folic acid,
about 90-230 mg calcium,
about 40-70 mcg selenium,
about 2.15-5 mg manganese,
about 200-650 mcg lutein, and
about 250-750 mcg lycopene.

According to one preferred embodiment, the nutritional supplement includes:
about 90 mg vitamin C, about 25 mcg vitamin K, about 600 mcg folic acid,
about 200 mg calcium, about 55 mcg selenium, about 2.3 mg manganese,
about 250 mcg lutein, and about 300 mcg lycopene.

Another to another preferred embodiment, the nutritional supplement is intended for adults over the age of 50 and includes:
about 90 mg vitamin C,
about 30 mcg vitamin K,
about 400-500 mcg folic acid, about 220 mg calcium, about 55 mcg selenium, about 2.3 mg manganese, about 250 mcg lutein, and about 300 mcg lycopene.

DEFINITIONS

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given the available tools.

The term "vitamin E" refers to natural vitamin E (dl-alpha tocopherol and salts thereof) and synthetic vitamin E (d-alpha tocopherol and salts thereof). When the vitamin E is naturally derived, the amount of vitamin E is about half that mentioned above (e.g., the weight ratio of vitamin D3, copper sulfate, chromium picolinate and natural vitamin E is preferably about 1540-5385 (IU):11.5-23.1 (mg):1-3.9 (mg):57.5231 (IU)).

As is known in the art, the supplement formulation of the present invention may contain an additional amount of each active ingredient as an overage to accommodate manufacturing processes and provide the indicated amount of each active ingredient to the body.

The following are nutrients which are generally considered important for maintaining good health.

Beta-carotene—may lower the risk of certain cancers as well as heart disease, and may protect against degenerative aspects of aging.

Biotin—is also known as vitamin H, and is used for cell growth, synthesis of fatty acids, and is associated with healthy skin and hair. Deficiencies may cause dry scalp, fatigue, nausea, vomiting and high cholesterol.

Calcium—helps in the maintenance of bones, teeth and gums. Calcium also assists in blood clotting and the transmission of nerve impulses. Calcium is also associated with lowering cholesterol, muscle growth and protein structuring. Deficiencies could lead to osteoporosis, hypertension and colon cancer.

Chloride—is an electrolyte which helps control the flow of fluid in blood vessels and tissues. It is also associated with the regulation of acidity in the body. Deficiencies may lead to an excessive loss of potassium from the body, weakness and lowered blood pressure.

Chromium—helps control insulin and is needed for energy and to maintain stable blood sugar levels. Deficiencies may cause anxiety, glucose intolerance, fatigue, and an increased risk of arteriosclerosis.

Copper—is necessary for the synthesis of hemoglobin, red blood cells and bones. It also helps the formation of elastin and collagen. Deficiencies may lead to increased blood fat levels.

Folic Acid—is necessary for DNA synthesis and red blood cell and amino acid formation. Deficiencies may cause anemia, osteoporosis, certain cancers as well as fatigue and acne.

Iodine—is used in the formation of hormones, and may prevent certain cancers. Deficiencies may cause constipation, obesity, weakness and metal health problems.

Lutein—is an antioxidant that contributes to improved eye health and protecting eyes from ultraviolet rays.

Lycopene—is an antioxidant believed to be useful for maintaining overall good health and healthy body parts.

Magnesium—assist in cellular metabolism, the production of energy and the formation of teeth and bone. It may also prevent the formation of kidney stones. Deficiencies may result in cardiovascular problems, fatigue, and seizure. Also associated with magnesium deficiencies are insomnia, poor memory, depression and hypertension.

Manganese—is needed for the manufacture of fat, sex hormones and breast milk. Deficiencies have been associated with poor bone growth, birth defects and paralysis, deafness and blindness in children.

Molybdenum—assists in breaking down sulfite toxins and in the prevention of cavities. May also prevent anemia and cancer. Deficiencies have been linked with impotence and toxin buildup that may lead to allergic reactions.

Niacin—is also known as vitamin B3, and is necessary for cell repiration, functioning of the nervous system and for the release of energy from carbohydrates, fats and proteins. Deficiencies may result in pellagra.

Pantothenic acid—is also known as vitamin B5, and is associated with hormone secretion, and for with the release from energy of carbohydrates, fats and proteins. Deficiencies may lead to frequent infection, fatigue, headaches and nausea.

Potassium—is used for growth, building of muscles, transmission of nerve impulses and for cardiovascular activities. Deficiencies have been linked to fatigue, leg cramps, acne, dry skin and irregular heartbeats.

Phosphorous—is used for the formation bone and teeth as well as various other metabolic activities. Deficiencies can cause painful bones, irregular breathing, fatigue, numbness and anxiety.

Riboflavin—is also known as vitamin B2, is needed for the metabolism of amino acids, fatty acids and carbohydrates. Deficiencies may result in eye problems, inflammation of the tongue and mouth and skin lesions.

Selenium—has been associated with increased antibody response to infection, and it may be useful in treating certain cancers as well as preventing heart attacks and strokes.

Thiamine—is also known as vitamin B1, and it may enhance blood circulation and formation. It is also necessary for maintaining a good immune system. It may also be associated with enhancement of memory and learning. Deficiencies may lead to beriberi, fatigue, constipation and edema.

Vitamin A—is used in the maintenance of healthy skin and the immune system. It is also associated with the prevention of cancers and other diseases. Deficiencies may lead to poor growth, eye problems and dry skin and hair.

Vitamin B-12—is required for the maintenance and formation of red blood cells, and it promotes growth. It is also believed to help prevent mental deterioration. Deficiencies may cause sore tongue, weakness, fatigue and weight loss.

Vitamin C—is necessary for the formation of collagen, neurotransmitters, and for the conversion of cholesterol. Vitamin C may also help in preventing cataracts, cancers and cardiovascular diseases. Deficiencies may cause scurvy, edema, weakness, bronchial infections and colds.

Vitamin D3—helps maintain healthy levels of calcium and phosphorous in the blood. Vitamin D3 is also associated with healthy bones, and a healthy heart and immune system. Deficiencies could lead to bone softening, muscle twitching and convulsions.

Vitamin E—is an antioxidant which is useful in preventing degenerative diseases such as heart disease, strokes, arthritis, senility, diabetes and cancer. Vitamin E has also been associated with good fertility, prevention of blood clots and healthy skin. Deficiencies may cause fatigue and premature aging.

Vitamin K—is necessary for blood clotting and may also reduce the severity of osteoporosis. Deficiencies may cause nosebleeds and internal hemorrhaging.

Zinc—is important for maintaining a healthy immune system, assisting in growth and maintaining muscles. Deficiencies may result in a weak immune system, stunted growth and fertility problems. A zinc deficiency may cause white spot under the fingernails.

Other Nutrients

The nutritional supplement may further include other nutrients. For example, the nutritional supplement may further comprise at least five nutrients selected from vitamin A, vitamin E, niacin, pantothenic acid, thiamine, riboflavin, vitamin B-12, biotin, iodine, phosphorous, magnesium and potassium chloride.

Preferably, the nutritional supplement further comprises:
about 1000-3500 IU vitamin A,
about 30-60 IU vitamin E,
about 20-40 mg niacin,
about 5-15 mg pantothenic acid, about 1-5 mg thiamine,
about 1-6 mg riboflavin,
about 1-30 mcg vitamin B12,
about 10-50 mcg biotin,
about 100-200 mcg iodine,
about 45-150 mg phosphorous,
about 20-130 mg magnesium, and
about 100-200 mg potassium chloride.

More preferably, the nutritional supplement further includes:
about 3500 IU vitamin A,
about 30 IU vitamin. E,
about 20 mg niacin,
about 10 mg pantothenic acid,
about 1.5 mg thiamine,
about 1.7 mg riboflavin,
about 6 mcg vitamin B12,
about 30 mcg biotin,
about 150 mcg iodine,
about 109 mg phosphorous,
about 100 mg magnesium, and about 152 mg potassium chloride.

Nutritional supplements for adults over the age of 50 preferably further include:
about 2500 IU vitamin A,
about 50 IU vitamin E,
about 20 mg niacin,
about 10 mg pantothenic acid,
about 1.5 mg thiamine,
about 1.7 mg riboflavin,
about 25 mcg vitamin B12,
about 30 mcg biotin,
about 150 mcg iodine,
about 110 mg phosphorous,
about 50 mg magnesium,
about 152 mg potassium chloride, and
no nutritionally significant amounts of iron and tin (i.e., less than 2 mcg).

These nutrients are known to be important for maintaining good health, as described above. The weight ratios of these nutrients are also believed to enhance the nutritional value derived from these nutrients. The nutritional supplement may further include beneficial herbal extracts including ginkgo and ginseng.

Formulations

The nutritional supplement is preferably a solid dosage form, such as a tablet (e.g., a chewable tablet) or capsule, which is suitable for once-a-day administration. Preferably, the nutritional supplement is a tablet.

The nutritional supplement may compose one or more excipients.

Suitable excipients include, but are not limited to, bulking agents (e.g., dibasic calcium phosphate (such as dibasic calcium phosphate USP, anhydrous) and microcrystalline cellulose), disintegrants (e.g., crospovidone), glidants (e.g., silicon dioxide), lubricants (e.g., magnesium stearate), and preservatives.

The nutritional supplement of the present invention may be prepared by methods known in the art.

The following examples illustrate the invention without limitation. All parts are given by weight unless otherwise indicated.

Example 1

The formulation of a nutritional supplement intended for regular use by a person younger than 50 years of age is shown below.

| Ingredient | Unit of measure | Amount |
| --- | --- | --- |
| Vitamin C | mg | 90 |
| Selenium | mcg | 55 |
| Vitamin E | IU | 30 |
| Thiamin | mg | 1.5 |
| Riboflavin | mg | 1.7 |
| Niacin | mg | 20 |
| Vitamin B6 | mg | 2 |
| Folic Acid | mcg | 400-500 |
| Vitamin B12 | mcg | 6 |
| Pantothenic Acid | mg | 10 |
| Biotin | mcg | 30 |
| Calcium | mg | 200 |
| Phosphorus | mg | 109 |
| Magnesium | mg | 100 |
| Vitamin D3 | IU | 400 |
| Vitamin A | IU | 2500 |
| Beta-Carotene! | IU | 1000 |
| Vitamin K | mcg | 25 |
| Iron | mg | 18 |
| Iodine | mcg | 150 |
| Zinc | mg | 11 |
| Copper | mg | 0.9 |
| Manganese | mg | 2.3 |
| Chromium | mcg | 35 |
| Molybdenum | mcg | 45 |
| Chloride | mg | 72 |
| Potassium | mg | 80 |
| Boron | mcg | 150 |
| Nickel | mcg | 5 |
| Silicon | mg | 2 |
| Tin | mcg | 10 |
| Vanadium | mcg | 10 |
| Lutein | mcg | 250 |
| Lycopene | mcg | 300 |

Example 2

The formulation of a nutritional supplement intended for regular use by a person older than 50 years of age is shown below.

| Ingredient | Unit of measure | Amounts |
| --- | --- | --- |
| Vitamin C | mg | 90 |
| Selenium | mcg | 55 |
| Vitamin E | IU | 50 |
| Thiamin | mg | 1.5 |
| Riboflavin | mg | 1.7 |
| Niacin | mg | 20 |
| Vitamin B6 | mg | 3 |
| Folic Acid | mcg | 400-500 |
| Vitamin B12 | mcg | 25 |
| Pantothenic Acid | mg | 10 |
| Biotin | mcg | 30 |
| Calcium | mg | 220 |
| Phosphorus | mg | 110 |
| Magnesium | mg | 50 |
| Vitamin D3 | IU | 500 |
| Vitamin A | IU | 1500 |
| Beta-Carotene | IU | 1000 |
| Vitamin K | mcg | 30 |
| Iodine | mcg | 150 |
| Zinc | mg | 11 |
| Copper | mg | 0.9 |
| Manganese | mg | 2.3 |
| Chromium | mcg | 45 |
| Molybdenum | mcg | 45 |
| Chloride | mg | 72 |
| Potassium | mg | 80 |
| Boron | mcg | 150 |
| Nickel | mcg | 5 |
| Silicon | mg | 2 |
| Vanadium | mcg | 10 |
| Lutein | mcg | 250 |
| Lycopene | mcg | 300 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, articles, publications, and test methods mentioned above are hereby incorporated by reference.

What is claimed is:

1. A nutritional supplement adapted for providing nutritional elements consisting of about 90 mg vitamin C, about 55 mcg selenium, about 30 IU vitamin E, about 1.5 mg thiamin, about 1.7 mg riboflavin, about 20 mg niacin, about 2 mg vitamin B6, about 400-500 mcg folic acid, about 6 mcg vitamin B12, about 10 mg pantothenic acid, about 30 mcg biotin, about 200 mg calcium, about 109 mg phosphorus, about 100 mg magnesium, about 400 IU vitamin D, about 2500 IU vitamin A, about 1000 IU beta-carotene, about 25 mcg vitamin K, about 18 mg iron, about 150 mcg iodine, about 11 mg zinc, about 0.9 mg copper, about 2.3 mg manganese, about 35 mcg chromium, about 45 mcg molybdenum, about 72 mg chloride, about 80 mg potassium, about 150 mcg boron, about 5 mcg nickel, about 2 mg silicon, about 10 mcg tin, about 10 mcg vanadium, about 500 mcg lutein, and about 600 mcg lycopene; and one or more excipients selected from the group consisting of bulking agents, disintegrants, glidants, lubricants, and preservatives.

2. A nutritional supplement adapted for providing nutritional elements consisting of about 90 mg vitamin C, about 55 mcg selenium, about 50 IU vitamin E, about 1.5 mg thiamin, about 1.7 mg riboflavin, about 20 mg niacin, about 3 mg vitamin B6, about 400-500 mcg folic acid, about 25 mcg vitamin B12, about 10 mg pantothenic acid, about 30 mcg biotin, about 220 mg calcium, about 110 mg phosphorus, about 50 mg magnesium, about 500 IU vitamin D, about 1500 IU vitamin A, about 1000 IU beta-carotene, about 30 mcg vitamin K, about 150 mcg iodine, about 11 mg zinc, about 0.9 mg copper, about 2.3 mg manganese, about 35 mcg chromium, about 45 mcg molybdenum, about 72 mg chloride, about 80 mg potassium, about 150 mcg boron, about 5 mcg nickel, about 2 mg silicon, about 10 mcg vanadium, about 250 mcg lutein, and about 300 mcg lycopene, wherein said supplement does not provide nutritionally significant amounts of iron and tin; and one or more excipients selected from the group consisting of bulking agents, disintegrants, glidants, lubricants, and preservatives.

3. A nutritional supplement adapted to provide nutritional elements consisting of vitamin D, copper, and chromium at a ratio of 330-1170 vitamin D (IU):1-2 copper (mg): 0.05-0.25 chromium (mg), zinc at a zinc to copper ratio of about 1.1-1.4, and one or more excipients selected from the group consisting of bulking agents, disintegrants, glidants, lubricants, and preservatives, wherein said vitamin D is cholecalciferol, said copper is copper sulfate and said chromium is chromium picolinate.

4. The nutritional supplement of claim 3, wherein said ratio is 667 vitamin D:1.5 copper:0.058 chromium.

5. The nutritional supplement of claim 3, wherein said ratio is 833 vitamin D:1.5 copper:0.075 chromium.

6. The nutritional supplement of claim 3, wherein said ratio is 667 vitamin D:1.5 copper:0.2 chromium.

* * * * *